(12) United States Patent
Samuel et al.

(10) Patent No.: US 7,214,823 B2
(45) Date of Patent: May 8, 2007

(54) HYDROXYCITRIC ACID COMPLEX METAL SALTS, COMPOSITION, AND METHODS

(75) Inventors: Philip Samuel, Bangalore (IN); Somasundaram Saravanan, Tamil Nadu (IN); Meyyappan Thangaraj, Tamil Nadu (IN)

(73) Assignee: Indfrag Limited, Karnataka State (IN)

( * ) Notice: Subject to any disclaimer, the term of this patent is extended or adjusted under 35 U.S.C. 154(b) by 378 days.

(21) Appl. No.: 10/822,867

(22) Filed: Apr. 13, 2004

(65) Prior Publication Data

US 2004/0259937 A1 Dec. 23, 2004

Related U.S. Application Data

(63) Continuation of application No. PCT/IN03/00192, filed on May 19, 2003.

(51) Int. Cl.
C07D 307/00 (2006.01)
C07C 59/265 (2006.01)

(52) U.S. Cl. ........................ 562/584; 549/308
(58) Field of Classification Search ........... 426/271; 424/494; 562/584; 549/308
See application file for complete search history.

(56) References Cited

U.S. PATENT DOCUMENTS

| | | | |
|---|---|---|---|
| 3,764,692 A | 10/1973 | Lowenstein | |
| 5,536,516 A | 7/1996 | Moffett et al. | |
| 5,612,039 A | 3/1997 | Policappelli et al. | |
| 5,656,314 A * | 8/1997 | Moffett et al. | 426/271 |
| 5,783,603 A | 7/1998 | Majeed et al. | |
| 6,160,172 A | 12/2000 | Balasubramanyam et al. | |
| 6,221,901 B1 | 4/2001 | Shrivastava et al. | |
| 6,395,296 B1 | 5/2002 | Balasubramanyam et al. | |
| 6,447,807 B1 * | 9/2002 | Clouatre et al. | 424/494 |
| 2003/0207942 A1 | 11/2003 | Bhaskaran et al. | |

FOREIGN PATENT DOCUMENTS

| | | |
|---|---|---|
| EP | 0 866 137 | 9/1998 |
| WO | 99/03464 | 1/1999 |

OTHER PUBLICATIONS

Tuček, et al., "Inhibitio of the Synthesis of Acetylocholinein RAT Brain Slices by (-)-Hydroxycitrate and Citrate", J. of Neurochemistry, vol. 36, No. 4, 1981, pp. 1331-1337.
Sugden, et al., "Proline and Hepatic Lipogenesis", Biochemica et Biophysica Acta, 798:368-373, 1984.
Řičný, et al., "Acetylcoenzyme A and Acetylcholine in Slices of Rat Caudate Nuclei Incubated eith (-)-Hydroxycitrate, Citrate and EGTA", J. of Neurochemistry, 39:668-673, 1982.
Palmer, et al., "Inhibition of lipogenesis by vasopressin and angiotensin II in glycogen-depleted hepatocytes", Bioscience Reports 3, 1063-1070, 1983.
Ohia, et al., Safety and mechanism of appetite suppression by a novel hydroxycitric acid extract (HCA-SX), 2002, Mol. and Cell. Biochem., 238:89-103.
Leonhardt, et al., "Hydroxycitrate has Long-Term Effects on Feeding Behavior, Body Weight Regain and Metabolism after Body Weight Loss in Male Rates", 2002, J. Nutr., 132:1977-1982.
Newton, et al., "The Effects of Specific Lipogenic Substrates and Metabolic Inhibitors on de novo Fatty Acid Synthesis in Isolated Hepatocytes from Chow-Fed Female Rats", 1980, Arch. Of Biochem. And Biophysics, 204:379-386.
Ishihara, et al., "Chronic (-)-Hydroxycitrate Administration Spares Carbohydrate Utilization and Promotes Lipid Oxidation during Exercise in Mice", 2000, J. Nutr., 130:2990-2995.
Hood, et al., "Inhibition by Potential Metabolic Inhibitors of in vitro Adipose Tissue Lipogenesis", 1985, Biochem. Physiol., 81B:667-670.
Fried, et al., "Role of fatty acid synthesis in the control of insulin-stimulated glucose utilization by rat adipocytes", 1981, J. Lipid Res., 22:753-762.
Chempakam, et al., "Slimming—The Garcinia Way", 2000, World, 27(6):35-36.
Wheeler, Thomas J., "Hydroxycitrate as a Weight Loss Ingredient", Health Care Reality Check, 1999.

* cited by examiner

Primary Examiner—Taylor Victor Oh
(74) Attorney, Agent, or Firm—Merchant & Gould P.C.

(57) ABSTRACT

Described are tri-, tetra-, and penta-metal complex salts of hydroxycitric acid, compositions containing the same, and methods of making the same, where the salt comprises at least three different metals selected from zinc, magnesium, sodium, potassium, and calcium.

9 Claims, No Drawings

HYDROXYCITRIC ACID COMPLEX METAL SALTS, COMPOSITION, AND METHODS

CROSS-REFERENCE TO RELATED APPLICATIONS

This application claims priority to PCT/IN03/00192 filed May 19, 2003 and designating the United States.

FIELD OF THE INVENTION

The invention relates to hydroxycitric acid salts. More specifically, the invention relates to hydroxycitric acid complex metal salts, compositions containing the same, and methods of making and using the same.

BACKGROUND OF THE INVENTION

*Garcinia acid* comprising (−)hydroxycitric acid (HCA), its lactone, and citric acid occurs in the fruit rind of *Garcinia* species (*Garcinia cambogia, G. Indica, G. atrovirdis*). In India the fruit is known by several local names (e.g., Kokum, Kodam Pulli, Uppige Hulli, etc.), and is used as a souring agent for pork and fish dishes. Traditionally, the extract of the fruit rind is used to improve digestion and in cooking, for the preparation of curries. The fruit rind of *Garcinia* is a rich source of (−)hydroxycitric acid, its lactone (10 to 30%), and citric acid.

(−)Hydroxycitric acid prevents the conversion of excess carbohydrates to fatty acids by inhibiting the actions of cytoplasmic (cytosolic) ATP-citrate lyase enzyme (D. Cloutre and M. E. Robenbaum, 1994, The Diet and Health Benefits of HCA) which plays key role in the conversion of carbohydrates to fatty acids and cholesterol (Sullivan et al., 1973, *Lipids*, 9:121,129).

Lewis et al., first isolated the lactone of (−)hydroxycitric acid from *Garcinia cambogia*. Pure (−)hydroxycitric acid is not stable and is converted to the more stable lactone form during processing. The free acid is stabilized by converting it into a salt form (e.g., sodium, potassium, calcium and zinc) by reacting the free acid with the respective base. Free (−)hydroxycitric acid can then be released when the salt is dissolved in an acid.

Some HCA compounds are known in the art. By way of example, EP 866137 relates to the preparation of calcium salt of HCA. However, since the calcium salt is insoluble in water, it is not preferred in formulating some products. As another example, U.S. Pat. No. 5,536,516 (Moffett et al.) describes a method to produce a liquid concentrate of HCA and its lactone, containing high concentrations of lactone compared to free HCA. However, this liquid HCA is not preferred because of its acidic nature and sour taste.

There is also described the preparation of soluble salts of (−) hydroxycitric acid. For example a tri-potassium salt of HCA was prepared by Lewis et al., (Methods in enzymology, vol. XIII, pp. 613–619 (Oct. 1, 1969), a soluble magnesium salt of HCA is described in U.S. Pat. No. 6,221,901 (Shrivastava et al.), and a soluble sodium and potassium salt of HCA is described in U.S. Pat. No. 6,395,296 (Balasubramanyam et al.). The recommended daily intake (RDI) of calcium, potassium, magnesium and zinc element is 1000 mg, 3500 mg, 400 mg and 15 mg respectively, and exceeding these amounts may create a risk of toxicity. Therefore, when these salts are used as individual salts (one metallic element in a given salt) there is risk of toxicity based on exceeding the RDI for the particular metallic element in the salt.

Accordingly, a need exists for other HCA salts and compositions containing the same.

SUMMARY OF THE INVENTION

The invention relates to complex metal salts of hydroxycitric acid, compositions containing the same, and methods of making the same. In an embodiment, the invention is a composition comprising a tri-, tetra-, or penta-metal complex salt of hydroxycitric acid wherein the salt comprises at least three different metals selected from zinc, magnesium, sodium, potassium, and calcium. In an embodiment, the invention is a process for preparing a tri-, tetra-, or penta-metal complex salt of hydroxycitric acid comprising preparing liquid hydroxycitric acid, reacting the liquid hydroxycitric acid with a mixture of bases comprising at least three of zinc, magnesium, sodium, potassium and calcium bases, to form a solution, and spray drying the solution to get the tri-, tetra-, or penta-metal complex salt of hydroxycitric acid.

The above summary of the present invention is not intended to describe each discussed embodiment of the present invention. This is the purpose of the figures and the detailed description that follows.

DETAILED DESCRIPTION OF THE INVENTION

The invention relates to tri-, tetra-, or penta-metal complex salts of hydroxycitric acid. In an embodiment, the present invention provides a composition comprising a complex metal salt of (−)hydroxycitric acid either alone or in combination with the lactone of HCA and citric acid, wherein the salt comprises mineral supplements such as sodium, potassium, calcium, magnesium and zinc on a Recommended Daily Intake (RDI) basis. In an embodiment, mineral supplements are incorporated as a single complex salt of HCA, such as (Ca,K,Mg,Zn)HCA. The complex metal salt is highly soluble in water, non-hygroscopic and stable in solution.

Complex metal salts of the invention can be used in dietary formulations. Such dietary formulations may be useful in promoting weight loss, preventing weight gain, or for other health benefits. The complex metal salts of the invention can also be used in dietary formulations that include other vitamins and minerals. The invention can help to provide the RDI of various metals including Na, K, Ca, Mg, and Zn along with a dose of hydroxycitric acid.

Another embodiment of the complex metal salt of the invention can be manufactured by keeping the pH of the final product below 4, in which case the product will contain a combination of HCA and the lactone of HCA. This low pH embodiment can be formulated in carbonated beverages in which the pH is maintained below 4 for stability and is suitable for use in food products without affecting their flavor or taste.

The complex metal salt of (−)hydroxycitric acid and its lactone is prepared from water extract of *Garcinia* and a mixture of bases selected from oxides, bicarbonates, carbonates, hydroxides of sodium, potassium, calcium, magnesium and zinc. Hydroxycitric acid is a tricarboxylic acid and therefore each HCA molecule can have only up to three different cations. However, some cations (such as the divalent cations $Ca^{++}$ and $Mg^{++}$) can bond with two different molecules of hydroxycitric acid.

Therefore, complex tetra or penta salts can be created using various cations and hydroxycitric acid. Embodiments of the complex metal salt of HCA can be prepared conveniently as highly soluble, partially soluble, or insoluble salt in water.

One embodiment of the invention that is essentially non-hygroscopic and stable in solutions has the composition as shown in Table 1 below:

TABLE 1

| Component of complex metal salt of HCA | wt. % of composition |
| --- | --- |
| (-)hydroxycitric acid (HCA), and/or lactone of (-)hydroxycitric acid | 40–75 0.1–30 |
| Citric acid | 1–5 |
| Sodium | 1–10 or preferably less than 1 |
| Potassium | 1–35 |
| Calcium | 1–20 |
| Magnesium | 1–15 |
| Zinc | 0.1–10 |

Embodiments of the complex metal salt of (-)hydroxycitric acid and its lactone can be manufactured by an economically viable process. In one embodiment, the *Garcinia* rind is extracted with demineralized water at room temperature. In contrast, the boiling or hot extraction used in the art gives an extract liquid that is enriched with unwanted water soluble components. In an embodiment, the invention minimizes the unwanted soluble matter by extracting the rind at room temperature. The extract liquid is treated with a calcium base to neutral pH to get insoluble calcium hydroxycitrate. The HCA content of this insoluble material is approximately 70%. If the neutralization is done at pH more than 7, the HCA content in the resulting insoluble salt will be only 50–60%.

The insoluble calcium salt of HCA is mixed with water and 10% sulphurous acid. This step removed the calcium as insoluble calcium sulphite. The pH is maintained at 3.0 to 3.5 during this operation. The art employs phosphoric acid in which case calcium cannot be removed as insoluble salt because both HCA and phosphoric acids are weak acids and an exchange reaction will not take place. The filtrate liquid, light brown in color, is treated with the preferred mixture of metal bases to neutral pH, treated with activated charcoal, filtered and spray dried to get white to off-white complex metal salt of HCA with or without the lactone of HCA. The resulting product is highly soluble in water (more than 20%), non-hygroscopic and stable in solution.

The present invention is described in further detail in the following examples, which are merely exemplary and are not intended to limit the scope of the invention.

EXAMPLE 1

Preparation of Liquid (-)Hydroxycitric acid and its lactone 600 kg of *Garcinia cambogia* rind (HCA content 20%) was loaded onto a counter current extractor. 2000 liters of demineralized water was charged and circulated at room temperature. 1600 liters of first wash liquid was collected with 4.5% HCA content. The spent material was again extracted two times with 1600 liters of demineralized water each time and the collected extract liquid was reused for subsequent batches. Only the first wash liquid from each extractor was used for further processing.

1600 liters of first wash liquid was pumped into a precipitation reactor to which 50 kg of calcium hydroxide was added to get 100 kg of dry insoluble calcium hydroxycitrate. A pH of 7.0 was maintained during the neutralization stage. HCA content of the insoluble calcium salt was 70.5%. 400 liters of demineralized water and 400 liters of 10% sulphurous acid were added to 100 kg of the insoluble calcium salt and mixed for 60 minutes. This step removed the calcium as insoluble calcium sulphite and gave 680 liters of clear light brown liquid HCA. This liquid HCA solution was used for producing the desired complex metal salts of *Garcinia* acid comprising (-)hydroxycitric acid, its lactone, and citric acid.

EXAMPLE 2

Preparation of an Embodiment of a Complex Metal Salt of HCA 400 liters of liquid HCA, as prepared in Example 1, was pumped into a 500 liter reactor. A solution of 7 kg of potassium hydroxide in 25 liters of demineralised water was added and stirred for 60 minutes at 70–80° C. Then a slurry of 6.8 kg of magnesium hydroxide and 3 kg of a zinc carbonate in 25 liters of demineralised water was added. Finally 4.3 kg of calcium hydroxide was added and stirred for 60 minutes. The neutralized solution was decolorized by adding 5 kg of activated charcoal. The resulting light yellow color solution was spray dried by maintaining the inlet temperature at 160° C. to give 54 kg of white crystalline powder with the composition as shown below in Table 2.

TABLE 2

| Component of complex metal salt of HCA | wt. % of composition |
| --- | --- |
| (-)hydroxycitric acid | 70.51% |
| Lactone of (-)hydroxycitric acid | 0.01% |
| Citric acid | 2.40% |
| Calcium | 4.30% |
| Potassium | 6.50% |
| Magnesium | 5.52% |
| Zinc | 2.35% |
| Sodium | 0.10% |

EXAMPLE 3

Preparation of Another Embodiment of a Complex Metal Salt of HCA 200 liters of liquid HCA, as prepared in Example 1, was pumped into a 500 liter reactor. A mixture of bases comprising 6.0 kg of sodium carbonate, 1.8 kg of magnesium hydroxide, 7.3 kg of calcium carbonate, 4.0 kg of potassium hydroxide and 1.24 kg of zinc carbonate was made into a slurry with 100 liters of demineralized water and added to the Liquid HCA, in small portions at a time, over a period of 6 hours. The neutralized solution was decolorized by adding 5 kg of activated charcoal. The resulting light yellow color solution was spray dried by maintaining the inlet temperature at 180° C. to give 28 kg of white crystalline powder with a composition as shown in Table 3 below.

TABLE 3

| Component of complex metal salt of HCA | wt. % of composition |
| --- | --- |
| (-)hydroxycitric acid | 57.67% |
| Lactone of (-)hydroxycitric acid | 7.16% |
| Citric acid | 1.90% |

TABLE 3-continued

| Component of complex metal salt of HCA | wt. % of composition |
| --- | --- |
| Calcium | 10.14% |
| Potassium | 8.37% |
| Magnesium | 2.86% |
| Zinc | 1.50% |
| Sodium | 8.44% |

EXAMPLE 4

Preparation of Another Embodiment of a Complex Metal Salt of HCA

A mixture of bases comprising 2.8 kg of magnesium hydroxide, 0.4 kg of zinc carbonate and 2.35 kg of calcium hydroxide was made into a slurry with 35 liters of demineralized water and added to 80 liters of liquid HCA (as prepared in Example 1), in small portions at a time, over a period of 4 hours. The partially neutralized solution was spray dried by maintaining the inlet temperature at 180° C. to give 10.8 kg of an off-white crystalline powder as shown in Table 4 below:

TABLE 4

| Component of complex metal salt of HCA | wt. % of composition |
| --- | --- |
| (-)hydroxycitric acid | 45.50% |
| Lactone of (-)hydroxycitric acid | 21.22% |
| Citric acid | 2.20% |
| Calcium | 11.60% |
| Magnesium | 10.46% |
| Zinc | 1.90% |

While the present invention has been described with reference to several particular implementations, those skilled in the art will recognize that many changes may be made hereto without departing from the spirit and scope of the present invention.

We claim:

1. A composition comprising a tri- or tetra-metal salt of hydroxycitric acid wherein the salt has at least three different metals selected from zinc, magnesium, sodium, potassium, and calcium.

2. The composition of claim 1, comprising a tetra-metal salt of hydroxycitric acid wherein the salt has at least four different metals selected from zinc, magnesium, sodium, potassium, and calcium.

3. The composition of claim 1, wherein the concentration of hydroxycitric acid is 40 to 75 wt %.

4. The composition 1 of claim, further comprising a lactone of hydroxycitric acid.

5. A process for preparing a tri- or tetra-metal salt of hydroxycitric acid having at least three different metals comprising:
preparing liquid hydroxycitric acid,
reacting the liquid hydroxycitric acid with a mixture of bases comprising at least three of zinc, magnesium, sodium, potassium, and calcium bases, to form a solution, and
spray drying the solution to afford the tri-, tetra-, metal salt of hydroxycitric acid.

6. The process of claim 5, wherein the temperature of spray drying is at about 150 to 2000 C.

7. The process of claim 5, the step of preparing liquid hydroxycitric acid comprising:
extracting hydroxycitric acid from *Garcinia* rind with demineralized water at room temperature to form an extraction solution,
treating the extraction solution with a calcium base until a neutral pH is reached to form insoluble calcium hydroxycitrate,
filtering out the calcium hydroxycitrate and then mixing the calcium hydroxycitrate with water and 10% sulphurous acid to form insoluble calcium sulfite, and
filtering out the calcium sulfite to leave liquid hydroxycitric acid.

8. A tri- or tetra-metal salt of hydroxycitric acid wherein the salt has at least three different metals selected from zinc, magnesium, sodium, potassium, and calcium.

9. The tri- or tetra-metal salt of hydroxycitric acid of claim 8 wherein the salt has two molecules of hydroxycitric acid.

* * * * *

UNITED STATES PATENT AND TRADEMARK OFFICE
CERTIFICATE OF CORRECTION

| | | |
|---|---|---|
| PATENT NO. | : 7,214,823 B2 | Page 1 of 1 |
| APPLICATION NO. | : 10/822867 | |
| DATED | : May 8, 2007 | |
| INVENTOR(S) | : Samuel et al. | |

It is certified that error appears in the above-identified patent and that said Letters Patent is hereby corrected as shown below:

Col. 6, line 12, claim 4: "composition 1 of claim, further" should read --composition of claim 1, further--

Col. 6, line 23, claim 5: "tri-, tetra-, metal" should read --tri- or tetra-metal--

Col. 6, line 26, claim 6: "150 to 2000 C." should read --150 to 200° C.--

Signed and Sealed this

Ninth Day of October, 2007

JON W. DUDAS
*Director of the United States Patent and Trademark Office*